United States Patent [19]

Newman

[11] Patent Number: 5,256,159
[45] Date of Patent: Oct. 26, 1993

[54] PERSONAL DEODORIZING APPARATUS FOR BODILY WASTE RESERVOIR

[75] Inventor: Arnold L. Newman, Kensington, Md.

[73] Assignee: Synexus Corporation, Bethesda, Md.

[21] Appl. No.: 835,821

[22] Filed: Feb. 18, 1992

[51] Int. Cl.$^5$ .............................................. A61M 1/00
[52] U.S. Cl. .................................... 604/317; 604/333; 604/332; 604/359; 55/385.4; 55/DIG. 35
[58] Field of Search ............... 604/312, 313, 317, 332, 604/333, 359; 55/385.4, 387, DIG. 32, DIG. 33, DIG. 34, DIG. 35

[56] References Cited

U.S. PATENT DOCUMENTS

| | | | |
|---|---|---|---|
| 3,952,727 | 4/1976 | Nolan | 604/333 |
| 4,224,610 | 9/1980 | Quinby | 604/318 |
| 4,331,137 | 5/1982 | Sarui | 128/200.16 |
| 4,350,507 | 9/1982 | Greenough et al. | 55/DIG. 35 |
| 4,451,258 | 5/1984 | Jensen | 55/385.4 |
| 4,911,699 | 3/1990 | Fenton | 604/333 |

Primary Examiner—Randall L. Green
Assistant Examiner—Paul Prebilic

[57] ABSTRACT

This invention relates to a bodily waste reservoir deodorizing apparatus and method for deodorizing odors from bodily waste reservoirs, such as ostomy appliances and diapers. The apparatus has a miniature fan that moves air through a deodorizing element, which may contain activated charcoal as a means for eliminating odors. It is often worn inconspicuously under the clothing close to the bodily waste reservoir, and serves to prevent social discomfort and embarrassment on the part of the wearer.

17 Claims, 2 Drawing Sheets

PERSONAL DEODORIZING APPARATUS FOR BODILY WASTE RESERVOIR

BACKGROUND OF THE INVENTION

This invention relates to an apparatus and method for diminishing the odor associated with bodily wastes. In particular it relates to an apparatus and method for diminishing odors that can emanate from bodily waste reservoirs such as ostomy appliances and diapers worn on or near the body.

U.S. Pat. No. 3,952,727 discloses a vent device associated with an ostomy appliance for venting gas from the appliance. The vent device includes a filter disk of matted fibers and charcoal particles that deodorizes vented gas.

U.S. Pat. No. 4,451,258 discloses an ostomy bag where vented gases are deodorized by controlling the rate of gas flow through an adjustable vent. The invention extends the effective transit time of vented gases through a flexible activated carcoal filter.

U.S. Pat. No. 4,203,445 discloses a gas venting filter assembly for use with collection devices such as a colostomy pouch. A slit aperture is described that prevents the loss of fluid from the pouch.

U.S. Pat. No. 4,911,699 discloses a deodorizing ostomy appliance where a deodorant such as activated charcoal is contained within a bag separate from the drainage receptacle but through which gas must pass when it is vented.

U.S. Pat. No. 4,224,610 discloses an alarm device that provides a warning when an enterostomy incontinence drainage pouch becomes filled. This allows the wearer to change, or empty the pouch to avoid leakage and breakage of the seal.

The above inventions are intended to control odors escaping from ostomy appliances either by deodorizing gases as they vent, or by signalling the ostomy wearer as to when the appliance needs to be changed or emptied. None of these inventions diminishes the odor of gases that have been incompletely deodorized during venting or of waste materials that have leaked from the appliance through small holes or an inadequate seal. None of these inventions diminishes odors that occur when an ostomy is removed or emptied. Furthermore, the above odor diminishing inventions are integral, structural elements incorporated into ostomy appliances and, as such, are ineffective in controlling odors when the ostomy appliance fails.

OBJECTS OF THE INVENTION

It is an object of the invention to produce an apparatus and method that diminishes objectionable and embarrassing odors emanating from a bodily waste reservoir located on or near the body.

A particular object of the invention is to provide a miniature deodorizing apparatus for use in association with a bodily waste reservoir such as an ostomy appliance or diaper and during surgery to prevent, limit, or diminish the emanation of unpleasant odors from the body and from these reservoirs.

Another object of the invention is to provide a miniature deodorizing apparatus for use in association with ostomies, diapers and during surgery to prevent, limit, or diminish the emanation of unpleasant odors due to the failure of these appliances.

It is a further object of the present invention to produce a deodorizing apparatus and method for use in association with an individual's body that decreases the emotional distress and embarrassment of an individual who has a health condition that causes objectionable and unpleasant odors.

It is an additional object of the present invention to produce an apparatus for use in association with an individual's body or a bodily waste reservoir to limit the emanation of odors from the body or bodily waste reservoir into the air outside the clothing and from being noticeable to other individuals.

SUMMARY OF THE INVENTION

The above and other objects of the present invention, which will become apparent as the description proceeds, are realized by a miniature deodorizing apparatus that is used by an individual to diminish the control odors originating from bodily waste reservoirs worn or held on or near the body. For the purposes of this invention, the term "bodily waste reservoir" is used to mean those reservoirs worn by an individual to temporarily collect and store bodily wastes before finally disposing of these wastes. For example, ostomy appliances and diapers are bodily waste reservoirs. The apparatus of this invention is usually made of a housing with an air inlet and an air outlet most often worn under the clothing close to the bodily waste reservoir, which is the potential source of odor. It includes an air moving element, such as a low noise, miniature fan, that moves air through a deodorizing element placed in an airflow passage, formed by the walls of the housing, that connects the inlet and outlet. The deodorizing element is usually a filter incorporating activated charcoal, sodium bicarbonate, or another porous, high surface area substance adsorbing or absorbing material through which air can pass. It adsorbs, absorbs or otherwise removes gaseous and other odoriferous substances from the moving air. It can be a disposable and replaceable element, enclosed within a frame, allowing easy replacement of an old, saturated element with a fresh one. A switch and speed control are provided so the wearer can operate the deodorizer continuously or intermittently at variable speeds. The apparatus can operate from a power source such as fixed capacity batteries or, most usually, rechargeable batteries. It is designed to be small and inconspicuous and is associated with the bodily waste reservoir by being held close to the source of odor, where it is most effective. For the purposes of this invention, inconspicuous means that, when the apparatus is worn under clothing, it is not apparent to an observer. Associating the apparatus with the bodily waste reservoir is done with a fastening, attachment or securing means such as a clip or clamp or by other fasteners and other attachment or securing means such as a belt, a garment, fabric hook and loop type fasteners commonly sold under the trademark Velcro TM, or by simply glueing the apparatus to the body. The bodily waste deodorizer is particularly effective when it is worn inconspicuously under clothing. In order to be inconspicuous, it is highly preferred that the thickness of the apparatus used under the clothing be less than two inches. Indeed, it is desirable that the device be less than one and a half inches or, even better, less than one inch thick. The fan and deodorizing element can be contained in a separate housing from another containing the batteries, switch and speed control. In this configuration, the two housings are electrically connected by a cable.

This apparatus deodorizes foul smelling, odoriferous air from the bodily waste reservoir by actively moving the air through a deodorizing element before it can disperse into the environment where it would be noticeable and unpleasant to others. Because the apparatus is often worn underneath clothing, an important feature of the invention is that it recirculates air under the clothing. It more effectively deodorizes the air by causing portions of it to pass many times through the deodorizing element.

The deodorizing apparatus is particularly useful to people who have had ostomy procedures performed. This kind of abdominal surgery produces an artificial opening, often called a stoma, that allows waste products to drain from the body. Usually, waste is collected in a drainage pouch or bag known as an ostomy appliance. Associated with this condition are the foul smelling and embarrassing odors of bodily wastes collected in the appliance. This problem is of particular concern when odoriferous air from within the bodily waste reservoir vents from the appliance, or when the appliance leaks or fails due to small holes or inadequate seal at the stoma or elsewhere, and odoriferous air from within the bodily waste reservoir is released into the environment. The possibility of this occurring is detrimental to a patient's confidence in social situations, and may even cause such patients to limit, and even avoid, social contact. This problem is described in an article about a cancer patient who had had a recent colostomy. "He worried about it leaking, about odor, about not being able to find a bathroom ... "(James T. Yenckel, "Fighting Back: Travel as Treatment", Washington Post, May 12, 1991, p. E1).

In contrast to deodorizing filters directly incorporated into ostomy appliances, the apparatus of the present invention is able to circulate and recirculate foul smelling air. Furthermore, because the apparatus of the present invention is separate from the ostomy appliance, it cannot be bypassed or otherwise caused to fail by a leak or other failure of the ostomy appliance. A deodorizing apparatus integrally incorporated with the ostomy appliance is subject to this problem. Thus, the present invention represents an important advance in handling ostomy related odors both in function and reliability. It can significantly decrease the anxiety and embarrassment of ostomy patients.

Patients with other health conditions can benefit from the miniature deodorizing apparatus of the present invention. For example, incontinent adults often wear diapers as reservoirs to collect bodily wastes. These patients, like ostomy wearers, also are concerned about the possibility of odors, and, thus, can also benefit from the ability of the present invention to diminish odors. Another use of the miniature deodorizing apparatus is to limit odors emanating from gangrenous flesh and bedsores, or during abdominal surgery.

BRIEF DESCRIPTION OF THE DRAWINGS

The above and other features of the present invention will be more readily understood when considered in conjunction with the detailed description and the accompanying drawings in which.

DETAILED DESCRIPTION OF THE PREFERRED EMBODIMENTS

Figure 1:
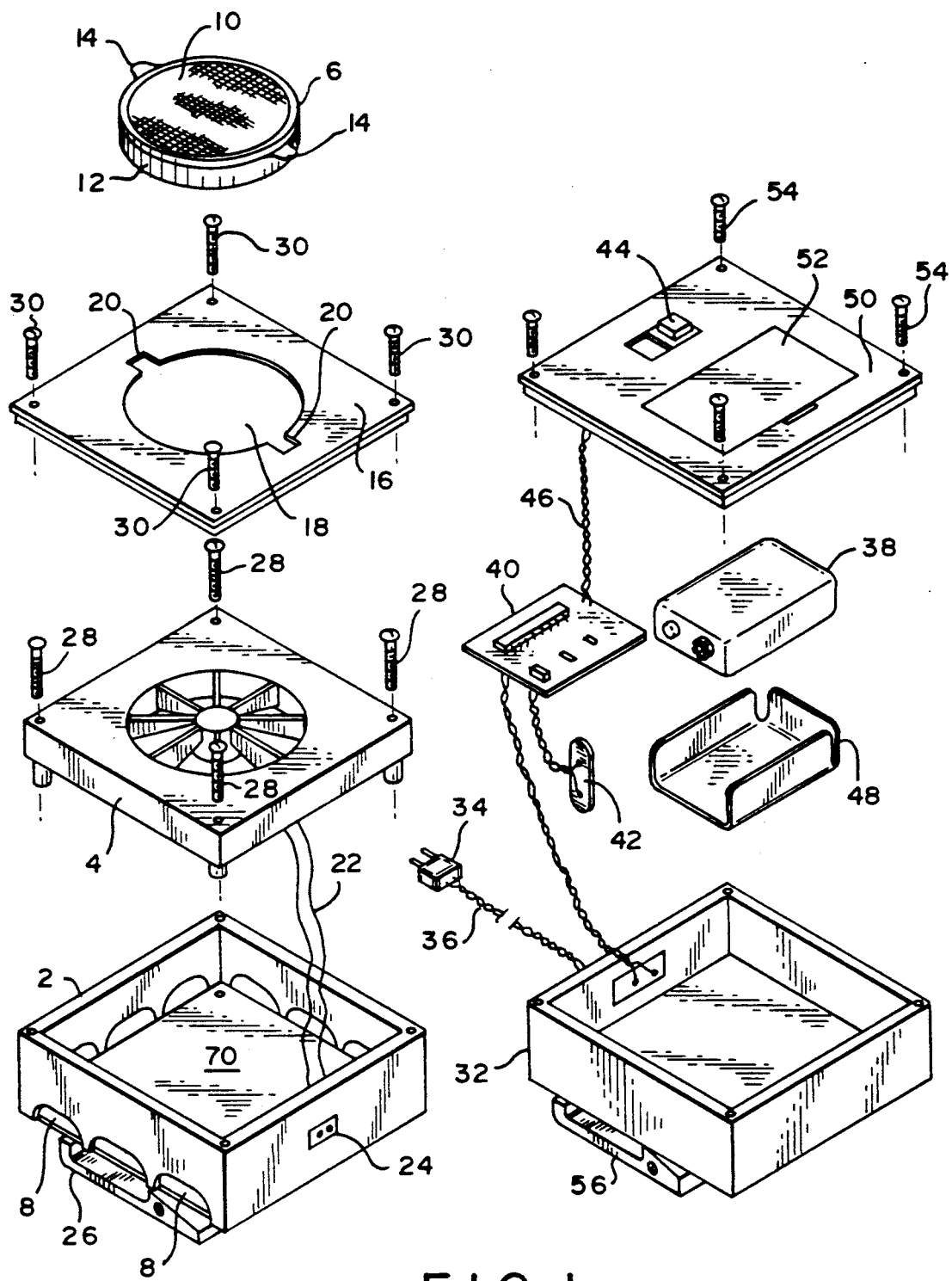
FIG. 1 is a partially exploded view in perspective illustrating the present invention.

A major function of the present invention is to provide a means for moving air under the clothing close to the body through a deodorizing material so as to diminish the presence of foul odors due to odoriferous air that can emanate from within a bodily waste reservoir. In FIG. 1, the apparatus is shown partitioned between two housings. A first housing 2 has an air moving means, in the form of fan 4, and a deodorizing assembly 6, as well as an inlet port 8 that is placed on the body or is supported by the body in association with the potential source of odor, such as an ostomy appliance, diaper, or other bodily waste reservoir. Inlet port 8 is shown as holes or openings in housing 2. Deodorizing assembly 6 is comprised of a deodorizing element 10 supported and enclosed by frame 12, which also forms tabs 14. The deodorizing element is preferably a porous material comprised of or containing activated charcoal, sodium bicarbonate ("baking soda"), or other odor removing material or combination thereof. For example, it can be activated charcoal filter. Activated charcoal and activated charcoal filters are known in the art for excellent deodorizing properties. The deodorizing element 10 can also contain for deodorizing purposes, in addition or instead of the ordor removing material, a pleasant smelling substance such as a perfume so that the deodorizing function or odor diminishing function of the apparatus can also be accomplished by masking foul odors with pleasant ones. There are many ways to disperse perfumes into the atmosphere, and these are well known in the art. One way, for example, is to immobilize the perfume within a solid matrix composed of a material chosen for its high rate of sublimation. The deodorizing element 10 is held or enclosed within frame 12, which is, for example, made of plastic or another flexible but hard material, forming deodorizing assembly 6, which is preferably a low cost, disposable item easily replaced when the deodorizing element 10 is saturated and no longer effective as a deodorizer. A first housing cover 16 for first housing 2 defines an outlet port 18, which is adapted to receive the deodorizing assembly. Deodorizing assembly 6 is placed into outlet port 18 with tabs 14 of frame 12 aligned with and fitted into tab notches 20 and is thus disposed in the airflow passage 70, which is the space formed by housing 2, connecting inlet port 8 and outlet port 18 and through which fan 4 moves air. Frame 12 is then twisted so that tabs 14 are forced out of alignment with tab notches 20 and held by a compression fit under the edge of outlet port 18, thus securing deodorizing element 10 in-line with outlet port 18, within the airflow passage 70. For the purposes of this invention, in-line denotes the path taken by air moving into, through and out of the airflow passage connecting the inlet port 8 and the outlet port 18. The path is not necessarily a straight one, and is defined by the geometry of the airflow passage 70. The deodorizing assembly 6 is removed from its position within the airflow passage 70, in-line with outlet port 18 by reversing the above procedure. In the preferred embodiment, fan 4 is an axial fan. These are usually low noise, direct current, brushless fans, commonly used to cool electronic equipment, and are commercially available in a wide variety of voltage and current ratings, dimensions, and air flow rates. Because the apparatus of the present invention is most often used to control potential odor sources beneath clothing where air volume is limited, it is not necessary to move large volumes of air for deodorization to occur. In fact, a considerable amount of recirculation of air through the deodorizing means occurs, and this optimizes the deodorization process. A consideration in the design of the preferred embodiment is to keep the size of the apparatus as small and light weight as possible. It is important that the apparatus, when worn, be as unnoticeable as possible to an observer. Furthermore, comfort to the wearer is enhanced by a light weight apparatus. Another design consideration is to choose a fan with a very low noise level. This prevents others from knowing of the wearer's problem and that the wearer is using the deodorizing apparatus. It is thus desirable that the rating for the fan noise is less than 33 dBA, and preferable that the rating for the fan noise be less than 30 dBA, as measured at a distance of one meter from the fan. Power conducting wires 22 conduct power to fan 4 and are connected to jack 24 in first housing 2. In the preferred embodiment, a first housing clip 26 attached to first housing 2, is used as a means for holding the inlet 8 of first housing 2 in close proximity to the potential odor source. In use, first housing clip 26 can be attached directly to a part of an ostomy appliance, a diaper, a belt, onto an article of clothing, or other structure close to the odor source. With fan 4 fastened inside first housing 2 by fan screws 28 and first housing cover 16 fastened to first housing 2 with first housing cover screws 30, first housing 2 constitutes an apparatus for use in association with a bodily waste reservoir, close to the source of odor. Fan screws 28 and housing screws 30 screw into tapped holes in first housing 2, that are not shown in FIG. 1, but whose design and use, as is readily appreciated, is well known in the art. In operation, housing 2 is electrically connected to a second housing 32 through jack 24, which is adapted to receive plug 34. Plug 34 terminates cable 36, which conducts power from a power source contained within second housing 32. The power source can be as simple as a battery, or it can be a battery associated with an electronic circuit such as a DC-to-DC converter or motor controller. As shown, the power source contained within second housing 32 is composed of a battery 38 and a power conditioning circuit 40, which is an electronic circuit such as a DC-to-DC converter/motor controller and may be of any well known design. The DC-to-DC converter converts the battery voltage to the optimum voltage for powering the fan 4. The power circuit 40 also contains a means for attachment to the battery 38 shown as battery plug/wire assembly 42, a connection to cable 36 through the wall of second housing 32, and a switch/speed control 44 connected to power circuit 40 by switch wires 46. It can also provide for a low battery indicator. Switch/speed control 44 is used both to turn the apparatus on and off as well as vary the speed of fan 4 with a slide potentiometer or the like with an off position, the variable resistance element of which is not shown, but is well known in the art. Battery 38 is received and held in second housing 32 by battery holder 48. Battery holder 48 and power conditioning circuit 40 are attached inside second housing 32 by glue. Second housing cover 50 supports switch/speed control 44, and also provides a port through to battery 38 to facilitate battery replacement. Battery access door 52 is connected to cover 50 by a hinge on one side and a clasp on the other. The hinge and clasp are well known in the art and are thus not shown. Second housing cover 50 is attached to second housing 32 with second housing screws 54. Second housing clip 56 is used to attach the second housing 32 to an article of clothing or some other support. For example, it can be attached to a belt, a pocket, or a loop extension of clothing. In operation, second housing 32 is usually, but not necessarily, placed remote from first housing 2. The apparatus is optimized by partitioning the air movement/deodorizing function of first housing 2 from the power control/supply function of second housing 32. First housing 2, which is usually worn beneath the clothing, is thus kept smaller, more unobtrusive, and less noticeable by its resulting decreased size.

Figure 2:
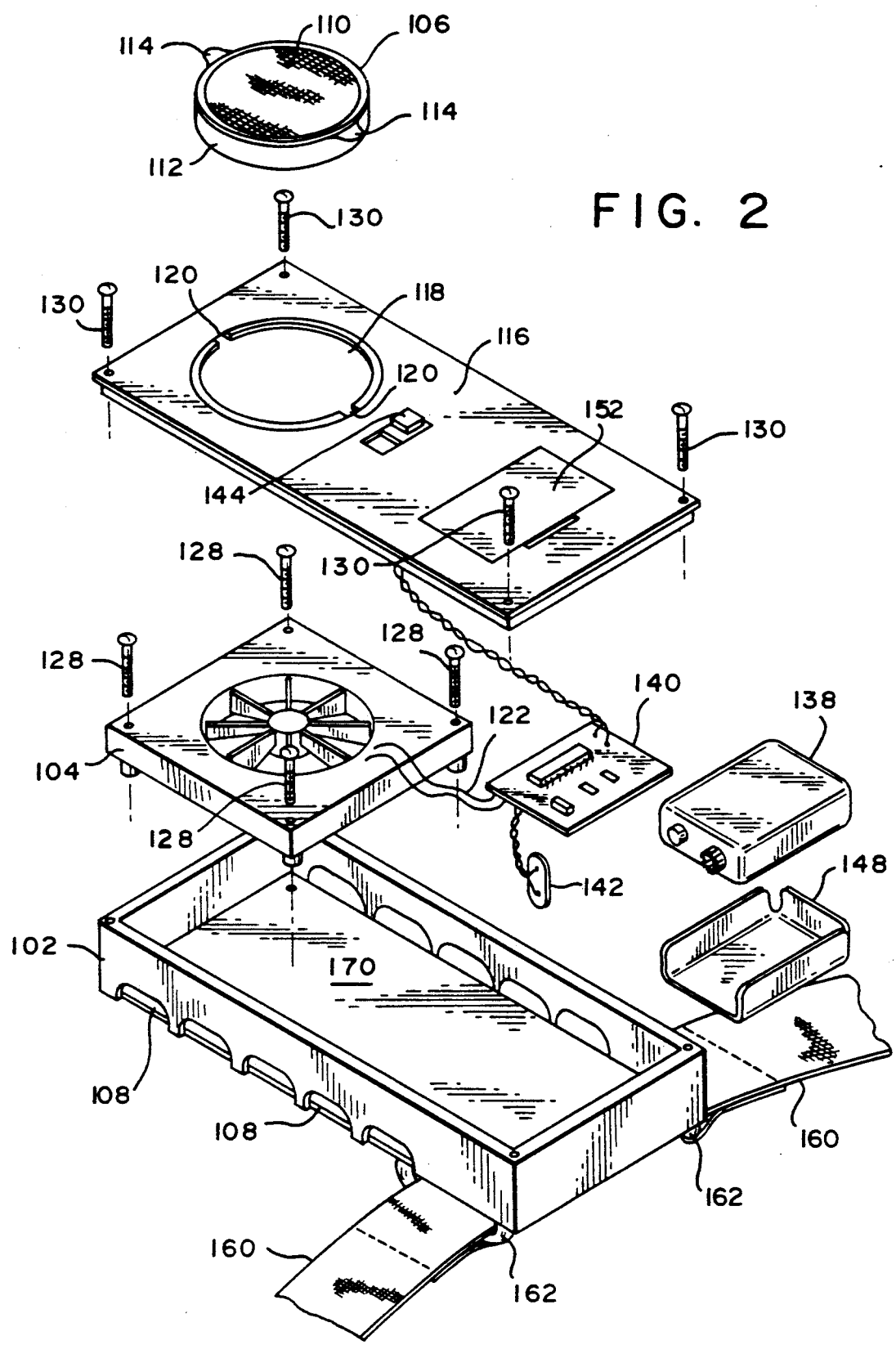
FIG. 2 is a partially exploded view in perspective illustrating another embodiment of the apparatus in accordance with this invention.

Another embodiment of the present invention is shown in FIG. 2. where the components are numbered in the "100" series, with the right two digits the same as the numbers of the corresponding component of FIG. 1. Here the apparatus, shown completely contained within one package, is used for moving air under the clothing close to the body through a deodorizing material so as to diminish foul odors that could potentially emanate from a bodily waste reservoir such as an ostomy appliance. A housing 102 has an air moving means, fan 104, and a deodorizing assembly 106, as well as an inlet port 108 that is placed in association with the bodily waste reservoir on the body and is supported on or by the body. Inlet port 108 is shown as holes or openings in housing 102. Deodorizing assembly 106 is configured as a deodorizing element 110 supported by frame 112, which also forms tabs 114. The deodorizing assembly 106 is the same as deodorizing assembly 6 shown in FIG. 1 and described above. Furthermore, deodorizing assembly 106 is used in the same way as deodorizing assembly 6 described above. Thus, deodorizing assembly 106 is placed into and is received by outlet port 118 which is defined by housing cover 116 so that tabs 114 of frame 112 are aligned with and fitted into tab notches 120. Deodorizing assembly 106 is then twisted so that tabs 114 are forced out of alignment with tab notches 120 and held by a compression fit under the edge of outlet port 118 thus securing deodorizing assembly 106 in-line with outlet port 118 within the airflow passage 170. Deodorizing assembly 106 is thus disposed in the airflow passage 170, which is the space formed by housing 102, connecting inlet port 108 and outlet port 118 and through which fan 104 moves air. The deodorizing assembly 106 is removed from its position within the airflow passage 170, in-line with outlet port 118 by reversing the above procedure. In this embodiment, fan 104 is the same as fan 4 of the embodiment shown in FIG. 1. Furthermore, the description and discussion about the fan 4 of the embodiment of FIG. 1 also pertains to fan 104 of the embodiment of FIG. 2 under discussion here, and thus, will not be repeated. Size, weight, noise level and other parameters discussed above also apply to the FIG. 2 embodiment. Power conducting wires 122 conduct power to fan 104 and are connected to power circuit 140, which is an electronic circuit such as a DC-to-DC converter/motor controller and may be of any well known design. The DC-to-DC converter converts the battery voltage to the optimum voltage for powering the fan 104. Power circuit 140 can also provide for a low battery indicator chosen from various known types commonly available. Battery 138 is connected to the power circuit 140 through battery plug/wire assembly 142, and is received and held in housing 102 by battery holder 148. Battery holder 148 and power circuit 140 are attached inside housing 102 by glue. Fan 104 is attached inside housing 102 by fan screws 128. Housing cover 116 is attached to housing 102 with housing screws 130. Fan screws 128 and housing screws 130 screw into tapped holes in housing 102, that are not shown in FIG. 2, but whose design and use, as is readily appreciated, is well known in the art. Housing cover 116 supports switch/speed control 144, and provides a port through to battery 138 to facilitate battery replacement. Switch/speed control 144 is used to both turn the apparatus on and off as well as vary the speed of fan 104. Battery access door 152 is connected to housing cover 116 by a hinge on one side and a clasp on the other. The hinge and clasp are well known in the art and are thus not shown. Belt 160 is attached to housing 102 by belt loops 162. The belt 160 is used to hold the apparatus close to the body in association with the bodily waste reservoir. In operation, the apparatus shown in FIG. 2 is usually used beneath the clothing, so that air having a foul odor from an ostomy appliance, for example, can enter inlet port 108 and be moved by fan 104 through airflow passage 170 and out outlet port 118, thus passing through deodorizing assembly 106, disposed in airflow passage 170 connecting inlet port 108 and outlet port 118. In operation, there is a tendency for air to recirculate through the apparatus before escaping through the clothing to the ambient air. This is also a feature of the embodiment of FIG. 1, and is a distinct benefit of the apparatus of this invention compared to deodorizing filters used, for example, as vents for ostomy appliances, which lack active air movement means such as a fan.

The particular elements of the embodiments are given as examples only. Variations of these elements are useful within the scope of the present invention.

Housing 2 of FIG. 1 and housing 102 of FIG. 2, as shown have covers, 16 and 116, respectively, which serve as top surfaces. Furthermore, as shown, housings 2 and 102 each have a bottom surface, and at least one side wall. In fact they each have four side walls as shown in the figures. The housings could be designed to have different configurations. For example, the shapes could be circular, with one curved wall serving as the side. Additionally, as shown in the figures, housing 2 and 102 in FIG. 1 and FIG. 2 respectively, have a plurality of holes that serve as an inlet (8 and 108 respectively), and a single large hole that serves as an outlet (18 and 118 respectively). Variations in the number of holes serving as inlet and outlet are within the scope of this invention. Furthermore, variations in the placement of the inlet and the outlet are also possible. For example, the outlet could be placed on the side and the inlet on the top surface of the apparatus. Another approach would be to have an air inlet on one side of the housing and an air outlet on the same or another side of the housing. If the inlet and outlet are on the same side of the housing, it is best that they not be adjacent each other. Keeping them remote from each other facilitates the introduction of new air to be deodorized. It is even possible to use the bottom surface as a place for an air inlet, air outlet, or both. In this case, if the housing were against the skin, it would raised by offsets or other means to facilitate airflow in and out of the apparatus.

Fan 4 of the embodiment of FIG. 1 and fan 104 of the embodiment of FIG. 2, within the design parameters discussed above, can be any of a variety of fans known in the art, or related air movement means. Centrifugal blower fans, propeller fans, impeller fans and axial fans as well as others known in the art that are consistent with parameters discussed above are applicable for the air moving purposes of this invention. Additionally, piezoelectric blower fans can also be used. Most commonly, the fan is an electric fan.

Switch/speed control 44 of FIG. 1 and 144 of FIG. 2 as shown is of a slide configuration. It allows the user to turn the apparatus on or off, and also to vary the speed of the fan. It is within the scope of this invention and also easily understood by those with ordinary skill in the art that these functions can be accomplished with different configurations. For example, a separate switch and variable resistor control can be provided. Another well known, commonly used configuration provides, on the same shaft, a control that incorporates a switch and a circular potentiometer. Power conditioning circuits 40 and 140 of FIG. 1 and FIG. 2 respectively are shown as a way to optimize power use, but other configurations that do not use such circuits are within the scope of this invention.

Variations in the positioning of certain elements in the apparatus are also possible. For example, the deodorizing assembly can be placed adjacent to the inlet or the fan, instead of adjacent to the outlet, as is shown in FIG. 1 and FIG. 2. It is thus placed in-line or within the airflow passage where a significant portion of air therein moves through the deodorizing element 10 of FIG. 1 or 110 if FIG. 2. The placement of the fan also can be varied. It can be on either side of the inlet or outlet, or, as shown in the figures, between the inlet and outlet in airflow passage 70 of FIG. 1 or 170 of FIG. 2. Depending on its placement, it is either pushing or pulling air through the apparatus. Elements can be partitioned differently from the configurations shown in the figures. For example, all elements of the apparatus except the inlet could be contained in a housing that is worn remote from the bodily waste reservoir. In this case, the inlet is kept close to the odor source, and communicates by a flexible tube or other air conducting means through to the housing, which is kept in a pocket, clipped to a belt, or otherwise supported by the clothing or body. Here the inlet and its communicating tube are configured for associating the deodorizing apparatus with the bodily waste reservoir. The clothing itself can be used as an air conducting means to allow air from under the clothing in need of deodorizing to be conducted to the inlet of the deodorizing apparatus which could, for example, be mounted on a belt, facing the body so it is still held inconspicuously under the clothing. In this case the air is drawn out from under the clothing and deodorized by the deodorizing apparatus and released into the ambient air.

Other fastening means known in the art can be used instead of screws or glue. These would include compression fit, brackets, and eyelet fasteners. Covers could, for example, be designed to snap into place and be held by compression. The deodorizing assembly 6 and 106 of FIG. 1 and FIG. 2 respectively can be received on the internal side of cover 16 of FIG. 1 or cover 116 of FIG. 2 so as to project out from port 18 of FIG. 1 or port 118 of FIG. 2. In this case the cover 18 or 118 of FIG. 1 or FIG. 2 respectively is hinged on one side and reversibly fastened on the opposite side. The deodorizing assembly 6 or 106 is held by compression of a rim flange beneath the lip of outlet port 18 or 118. It is easily replaced with a new assembly by unfastening the cover 18 or 118 of FIG. 1 and FIG. 2 respectively.

An important feature of this invention is that it provides a means for removably attaching, fastening, or securing the inlet or the inlet, in conjunction with the apparatus, close to the bodily waste reservoir, which is most usually under clothing. The apparatus can be fastened, attached, or secured to an article of clothing, the bodily waste reservoir, and even the body itself. Thus the deodorizing apparatus is removably associated with the bodily waste reservoir. In FIG. 1 a clip means is shown and in FIG. 2 a belt is shown. Other attachment means for fastening or securing known in the art are also useful. These include the use of adhesives for holding the device on the body, directly on the bodily waste reservoir, or on a garment or an article of clothing such as a belt. Removable attachment, fastening or securing means such as fabric hook and loop type fasteners commonly sold under the trademark Velcro TM are also possible. Furthermore, a pocket can be provided on the underside of clothing to accommodate the apparatus. Specially designed undergarments can also be used to hold and position the apparatus for effective deodorizing function.

Activated charcoal is known in the art to adsorb or absorb a large variety of gaseous and other substances, even when these substances are present in very low concentrations. Other materials such as powdered sodium bicarbonate are known to function similarly. Deodorizing element 10 in FIG. 1 or 110 in FIG. 2 can be constructed in a number of different ways so as to allow air to pass through easily and thus to be pervious to air. For example, it can be formed from a porous organic material that has been converted to activated carbon by a heat process or other process to make an activated charcoal filter. Here, porosity is maintained. Another approach is to use activated charcoal in a particulate form such as pellets, granules, or powder sandwiched in a layer or layers between two or more sheets of porous material, which can be, for example, filter paper that has been fastened at the edges. This also results in an activated charcoal filter. Particulate sodium bicarbonate that is powdered or granular can also be used with this sandwich approach. Although the above two configurations of deodorizing element 10 or 110 are particularly well suited for producing a disposable deodorizing assembly 6 or 106, another approach would be to have the deodorizing assembly define a space between two opposing, porous faces through which air can easily pass. One of the faces is removable to allow the addition or removal of activated charcoal pellets or powder, or sodium bicarbonate powder.

Although various specific materials and constructions have been presented herein, it is to be understood that these are for illustrative purposes only. Numerous modifications and adaptations will be readily apparent to those of ordinary skill in the art. Accordingly, the scope of the present invention should be determined by reference to the claims appended hereto.

I claim:

1. A method for deodorizing odors from a bodily waste reservoir containing odoriferous air, comprising the steps of:
   a. providing a housing defining an air inlet, an air outlet, and an airflow passage connecting said inlet and said outlet, said housing having a fan for moving air into said inlet, through said airflow passage and out said outlet;
   b. providing a deodorizing means disposed within said airflow passage;
   c. securing said housing inconspicuously under clothing in removable association with said bodily waste reservoir;
   d. moving said odoriferous air with said fan into said inlet;
   e. contacting said odoriferous air with said deodorizing means to remove odors in the air; and
   f. moving the thus deodorized air out said outlet.

2. A bodily waste reservoir deodorizer, comprising:
   a. at least a first housing defining an air inlet, an air outlet and an airflow passage connecting said inlet and said outlet;
   b. said first housing having a fan for moving air into said inlet, through said airflow passage, and out said outlet;
   c. a deodorizing means disposed within said airflow passage for deodorizing air entering said inlet;
   d. a means for removably associating said bodily waste reservoir deodorizer with a bodily waste reservoir; and
   e. said bodily waste reservoir deodorizer sized to be worn under clothing of an individual.

3. The bodily waste reservoir deodorizer as recited in claim 2 further comprising a second housing, remote from said first housing, electrically connected to said first housing, said second housing containing at least one of a power source, an electronic circuit, a switch, or a speed control.

4. The bodily waste reservoir deodorizer as recited in claim 2 wherein said means for removably associating said bodily waste reservoir deodorizer with said bodily waste reservoir is adapted to secure the first housing to one of a living body, said bodily waste reservoir, or an article of clothing.

5. The bodily waste reservoir deodorizer as recited in claim 2 wherein said deodorizing means comprises an least one of activated charcoal, sodium bicarbonate, or perfume.

6. The bodily waste reservoir deodorizer as recited in claim 2 wherein said housing is less than two inches in thickness.

7. The bodily waste reservoir deodorizer as recited in claim 2 wherein said housing is less than one inch thick.

8. The bodily waste reservoir deodorizer as recited in claim 2 wherein said fan is rated to have a noise level, measured at one meter from said fan, of less than 33 dBA.

9. A bodily waste reservoir deodorizer for deodorizing odors produced by the human body, comprising:
   a. at least a first housing having a top surface, a bottom surface, and at least one side wall wherein said housing has at least one opening serving as an air inlet, and at least one opening serving as an air outlet;
   b. an airflow passage within said first housing, connecting said inlet and said outlet;
   c. an electric fan mounted within said housing for moving air into said inlet, through said airflow passage, and out said outlet;
   d. an activated charcoal filter disposed within said airflow passage and through which said moving air passes so as to deodorize said moving air;
   e. a fastener for removably associating said bodily waste reservoir deodorizer with a bodily waste reservoir; and
   f. said bodily waste reservoir deodorizer sized to be worn inconspicuously under clothing.

10. The bodily waste reservoir deodorizer as recited in claim 9 further comprising a second housing, remote from said first housing, electrically connected to said first housing, said second housing containing at least one of a power source, an electronic circuit, a switch, or a speed control.

11. The bodily waste reservoir deodorizer as recited in claim 9 wherein said fastener for removably associating said bodily waste reservoir deodorizer with said bodily waste reservoir is adapted to secure the housing to one of a living body, said bodily waste reservoir, or an article of clothing.

12. The bodily waste reservoir deodorizer as recited in claim 9 wherein said housing is less than two inches in thickness.

13. The bodily waste reservoir deodorizer as recited in claim 9 wherein said first housing is less than one inch thick.

14. The bodily waste reservoir deodorizer as recited in claim 9 wherein at least one of said air inlet or said air outlet is on a side of said first housing and the other of said inlet or said outlet is on a top surface of said housing.

15. The bodily waste reservoir deodorizer as recited in claim 9 wherein said air inlet is on at least a one side of said first housing and said air outlet is on at least a one side of said first housing remote from said air inlet.

16. The bodily waste reservoir deodorizer as recited in claim 9 wherein at least one of said air inlet or said air outlet is on a side of said first housing and the other of said inlet or said outlet is on a bottom surface of said first housing.

17. The bodily waste reservoir deodorizer as recited in claim 9 wherein said fan is rated to have a noise level, measured at one meter from said fan, of less than 33 dBA.

* * * * *